United States Patent [19]

Lee

[11] Patent Number: 5,733,540
[45] Date of Patent: Mar. 31, 1998

[54] PROTECTION FROM VIRAL INFECTION VIA COLONIZATION OF MUCOSAL MEMBRANES WITH GENETICALLY MODIFIED BACTERIA

[76] Inventor: Peter Poon-Hang Lee, 1130 Welch Rd., Apt. 313, Palo Alto, Calif. 94304

[21] Appl. No.: 401,070

[22] Filed: Mar. 8, 1995

[51] Int. Cl.$^6$ .................................................. A01N 63/00
[52] U.S. Cl. ...................... 424/93.1; 424/93.2; 424/93.4; 424/93.45
[58] Field of Search ............................ 435/172.1, 172.2, 435/172.3, 173.1, 173.8, 235.2, 252.3, 244, 252.1; 424/93.1, 93.2, 93.4, 93.45

[56] References Cited

U.S. PATENT DOCUMENTS 5,348,867  9/1994  Georgiou et al.
5,531,988  7/1996  Paul ........................................ 424/93.4

FOREIGN PATENT DOCUMENTS

WO 93/18161  9/1993  WIPO.

OTHER PUBLICATIONS

Marshall, Science, 269: 1050–1055, 1995.
Int.J.Tiss REACXIII(2) 115–122 (1991), "Lactobacilli in Relation to Human Ecology and Antimicrobial Therapy," 1991 Bioscience Ediprint, Inc.
Gastroenterology 1992;102:875–878, "Fecal Recovery in Humans of Viable Bifidobacterium sp Ingested in Fermented Milk," 1992 by the American Gastroenterological Association.
Am J Clin Nutr 1992;55:78–80, "Survival bifidobacteria ingested via fermented milk during their passage through the human small intestine: an in vivo study using intestinal perfusion $^{1-4}$," 1992 American Society for Clinical Nutrition.
Human Health: The Contribution of Microorganisms Formulation, Production and Marketing of Probiotic Products, "Commercial Aspects of Formulation, Production and Marketing of Probiotic Products," Chapter 10, S. Lauland.

Primary Examiner—Suzanne E. Ziska
Attorney, Agent, or Firm—Townsend and Townsend and Crew LLP

[57] ABSTRACT

This invention relates to the use of genetically modified, non-pathogenic bacteria on the mucosal surfaces of a host to inhibit infection by specific viruses at mucosal surfaces. Specifically, non-pathogenic bacteria are modified to acquire the capacity to bind and functionally inactivate specific viruses. Further manipulations are devised to ensure the persistent colonization of said bacteria on the desired mucosal surface of a host. The capacity to bind a pathogen by said bacteria may be accomplished through the expression on the bacterial surface of a molecule, either a polypeptide or carbohydrate moiety, which binds specifically to a molecule on the target virus. Such a capacity may be conferred upon said bacteria via genetic manipulations. Genetic manipulations of said bacteria may be carried out in vitro and the genetically-engineered bacteria applied onto the desired mucosal surface of a host, or genetic material may be directly introduced into bacteria which are already resident on the desired mucosal surface of a host through a vector.

28 Claims, 1 Drawing Sheet

PROTECTION FROM VIRAL INFECTION VIA COLONIZATION OF MUCOSAL MEMBRANES WITH GENETICALLY MODIFIED BACTERIA

BACKGROUND OF THE INVENTION

1. Field of the Invention

This invention relates to the manipulation of the bacterial flora normally residing harmlessly on mucosal surfaces to interfere with infectious processes. Specifically, this invention provides for modification of non-pathogenic floral bacteria to confer upon them the capacity to bind to (and functionally inactivate) specific viruses. Although this disclosure describes a method of preventing infection by viruses which infect through mucosal surfaces, the skilled practitioner will recognize that the invention may potentially be applied to any pathogen which infects at a mucosal surface, including bacteria, fungi, and parasites.

2. Information Disclosure

Cytoplasmic expression of heterologous proteins by bacteria has been widely practiced for well over two decades. However, expression of heterologous proteins specifically onto the external surfaces of bacteria has been achieved only in the past few years. Surface expression systems for both gram-positive and gram-negative bacteria are known, e.g., U.S. Pat. No. 5,348,867, and WO 93/18163.

SUMMARY OF THE INVENTION

This invention provides for a method of protecting an animal from a viral infection comprising contacting a mucosal surface of the host with an amount of transformed bacteria sufficient to colonize the mucosal surface and to protect the animal from viral infection, said bacteria having been transformed with genetic material so as to confer upon the bacteria the capacity to bind the virus. More specifically, this invention provides for transformed bacteria that bind virus or other pathogens using naturally occurring receptors, domains of receptors or antiviral antibodies that are the products of the genetic material.

Preferred hosts are humans. Where the naturally occurring receptors are known, genes encoding those receptors may be used to transform the bacteria. When the specific viral/host receptors are not known, genes encoding antiviral antibodies or fragments thereof may be used to transform the bacteria. For example, for retroviruses that are covered with human leukocyte antigens [HLA DR], antibodies against these antigens are useful. Accordingly, this invention can be used against rotavirus, papillomavirus, adenovirus, respiratory syncytia virus, corona virus, cytomegalovirus, coxsackievirus, echovirus, hepatitis A virus, rhinovirus, human immunodeficiency virus, poliovirus, Epstein-Barr virus, parainfluenza virus and herpes simplex virus using bacteria able to bind to conserved determinants on their respective capsids.

The bacteria may also be modified to express a specific carbohydrate moiety which serves as the receptor for the virus onto its normal surface proteins. For example the bacteria may be transformed with genetic material which causes the addition of sialic acid which permits the bacteria to bind to an influenza virus.

The bacteria may also be modified to cause fusion between the bacterial membrane and the viral envelope, if present. An example is the transformation of bacteria so that it can fuse with bound viral particles through a fusogenic domain engineered into the virus-binding polypeptide.

Colonization of mucosal membranes is an essential element of this invention and it is preferred that the transformed bacteria is conferred with sufficient selective advantage to permit it to compete effectively with resident bacteria to allow said transformed bacteria to successfully colonize and survive indefinitely on a selected mucosal surface. One selection advantage is an enhanced ability to adhere to a host mucosal surface through a domain in the heterologous protein which binds to a determinant on a selected mucosal surface. Selective advantage might also be conferred by the use of antibiotic resistant transformed bacteria where antibiotics are co-administered with the transformed bacteria. Other advantages include the use of products that degrade the biofilm of the mucosal membrane. Such products would include DNAses, peptidases, and hyaluronidases.

Preferred mucosal surfaces are in the following organs: nasopharynx, oropharynx, esophagus, small intestines, large intestines, rectum, vagina, and penis.

Transformed bacteria are applied to a mucosal surface through the use of a liquid solution, foam, suppository, sponge, or capsule. Where the target mucosal layer is in the vagina, the bacteria can be transformed to target sexually transmitted pathogens such as but not limited to HIV, HPV, HSV, gonorrhea, syphilis and chlamydia. Nonbacteriocidal spermicides might be co-administered with the bacteria.

The invention also embraces a means to prevent the spread of a viral pathogen from an infected individual to others with transformed bacteria by administering an amount of transformed bacteria sufficient to colonize the mucosal surfaces of the infected individual wherein said bacteria bind and inactivate infectious viral particles exiting the infected host. The modifications and targets being as stated above.

The transformation of the bacteria can be either in vitro or in vivo whereby the resident musocal bacterial flora of a host is transformed with a desired foreign genetic material by directly introducing into resident microfloral bacteria a genetic vector said vector conferring the ability of the bacteria to bind and inactivate viral pathogens of the host and thereby affording protection of the host from infection by the viral pathogen. Examples of vectors include replication defective bacteriophage.

The invention further includes inactivating infectious viral particles in suspect water supplies by the addition of engineered bacteria capable of binding and irreversibly inactivating specific viruses.

In addition to methods, this invention also embraces compositions of matter comprising a bacteria selected for its ability to colonize the mucosal membrane of a host and transformed to express a host receptor or an antibody specific for a target virus on its cell surface in an amount sufficient to bind and inactivate the target virus. The preferred compositions are as described above for the various methods.

DETAILED DESCRIPTION

Figure 1:
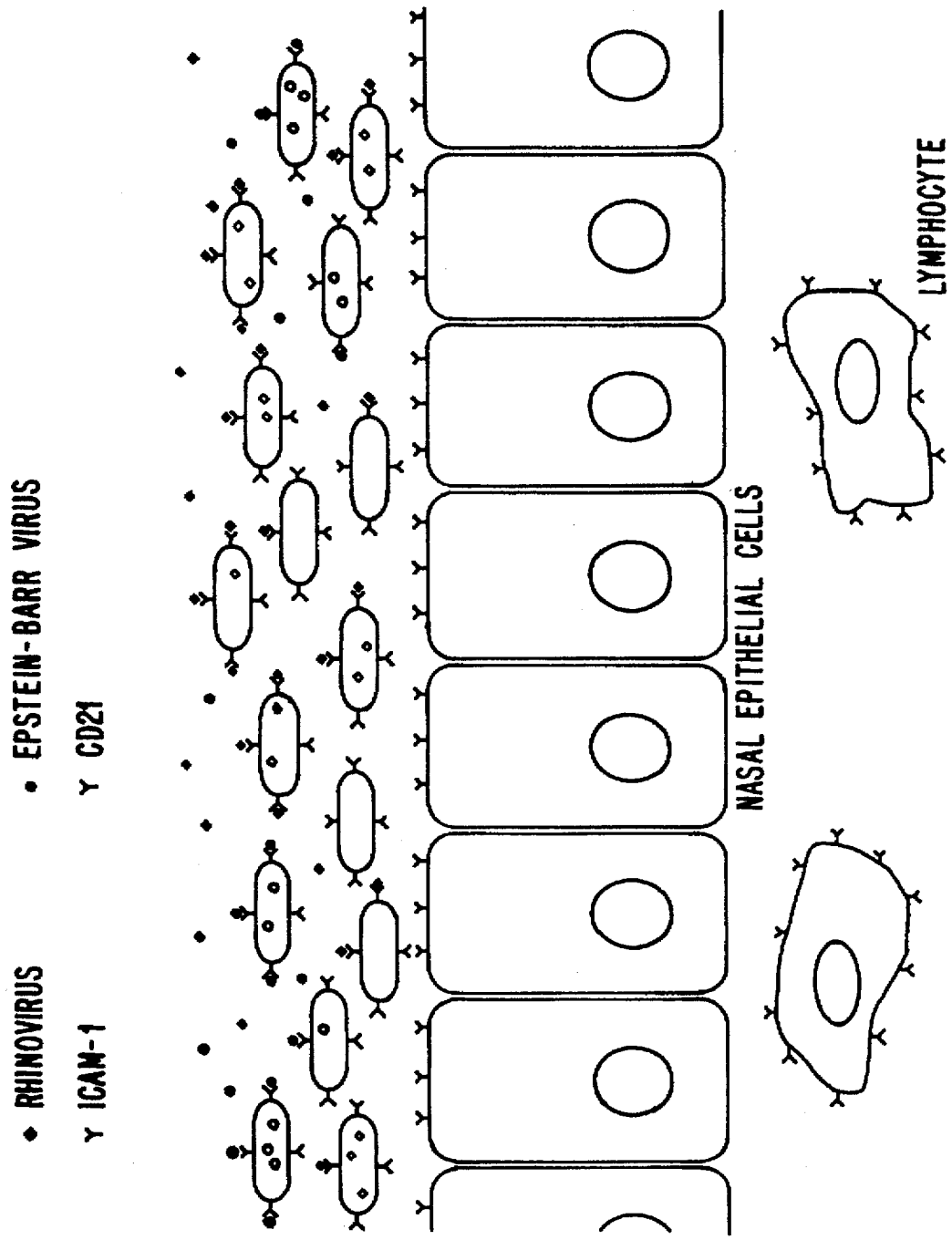
FIG. 1 illustrates the ViroShield™ concept. Viruses normally gain entry into a host by binding to specific receptors expressed on the host cell surface. Expression of the same receptors on the surface of bacteria on mucosal surfaces will cause the majority of the viruses to bind to the bacteria instead, where they are functionally inactivated, thus preventing infection of the underlying host cells.

A. Introduction.

Most viruses infect via mucosal surfaces. A review of this process can be found in Murray, P. R., et al., *Medical Microbiology*, 2nd Edition, (hereinafter Murray, et al., 1994). The creation of a virus blocking bacterial flora in the mucosal surfaces by allowing colonization of bacteria transformed to bind and inactivate virus is particularly advantageous. Colonization of mucosal layers is a routine undertaking. Most mucosal layers are typically teeming with bacteria, and changes in flora attendant to pathogenic bacterial infection and administration of antibiotics is a common event. The routine nature of the floral changes on mucosal surfaces is a key advantage of the invention. The following discussion will also provide means to enhance the ability of transformed bacteria to colonize mucosal layers.

B. General methods

The techniques of amplification of genetic sequences with the polymerase chain reaction (PCR), cutting and splicing DNA into plasmids, transformation of bacteria with plasmids, and assays for antibody binding are all well known biotechnology methods and detailed descriptions of these methods can be found in a number of texts including *Protocols in Molecular Biology, Molecular Biology of the Cell*, and Sam brook, et al., *Molecular Cloning-A Laboratory Manual*, Cold Spring Harbor Laboratory, Cold Spring Harbor, N.Y. 1989.

C. Viral targets.

The following is a list of viral targets. They are categorized by their respective organs of entry.

1. Upper respiratory tract (URT).

A large number of viruses infect the naso- and oropharynx, either via air droplets or direct contact. These include human rhinoviruses (HRV), adenovirus, coxsackievirus, influenza, parainfluenza, respiratory syncytia virus (RSV), Epstein-Barr Virus (EBV), and cytomegalovirus (CMV).

2. Gastrointestinal (GI) tract.

These viruses include rotavirus, Norwalk agent, hepatitis A (HAV), poliovirus and other picornaviruses.

3. Vaginal: human immunodeficiency virus (HIV), human papilloma virus (HPV), herpes simplex virus (HSV) 2, CMV, hepatitis B virus (HBV), hepatitis C virus (HCV).

D. Viral receptors.

A virus must enter a host cell to replicate. To enter a cell, viruses require surface receptors on the host cell (Murray, et al., 1994). More specifically, the virus must first bind to a molecule on the surface of the target cell. The receptors for a number of viruses have been determined in recent years. The following is a representative list and is not meant to be a limitation of the invention.

1. HRV, major group→ICAM-1, domains 1 and 2 (Lineberger, D. W., et al., *Virus Research*, 24(2):173–86, 1992.)
2. Influenza virus→sialic acid
3. HIV→CD4, domains 1 and 2
4. Poliovirus→PVR (poliovirus receptor, an immunoglobulin superfamily protein)
5. EBV→CD21 (complement receptor 2, the receptor for C3d)
6. HSV→heparin sulfate
7. HBV→IgA receptor
8. Adenovirus→Vitronectin receptor E. Mucosal Surfaces are Normally Colonized by Bacterial Flora (Murray, et al., 1994)

The upper respiratory tract (URT) consists of the nasopharynx, oropharynx (oral cavity and larynx), paranasal sinuses, and the middle ear. The paranasal sinuses and the middle ear are normally sterile. However, the stratified squamous epithelium of the naso- and oropharynx are teeming with a varied microbial flora. The microflora of the nose consists mainly of coagulase-negative staphylococci, with some diphtheroids (aerobic and anaerobic), and non-hemolytic streptococci. The most prominent members of the flora of the mouth and pharynx are the alpha streptococci. Some gram-negative anaerobes (esp. Bacteriodes) and other cocci are also found.

The colon contains the largest total population of bacteria of any mucosal surface in the human body. It is estimated that $>10^{11}$ bacteria/g of colonic content exists in healthy individuals, representing over 400 species. Anerobic bacteria outnumber aerobic ones by a factor of 100–1,000. Bacteroides is the predominant genus. Bifidobacterium, Enterobacteriaceae, Streptococci, and Lactobacilli are also prominent. The small intestine is populated by a similar profile of organisms as the colon, but at much lower numbers. The stomach and proximal small intestine are nearly sterile, while the distal small intestine contains approximately 1/10 of the bacterial content of the colon.

The vaginal mucosa is also colonized by a large number of bacteria. Lactobacilli are the predominant species in the normal menarchal vaginal microflora, being present in nearly 100% of normal women. Lactobacilli are facultative anaerobes, and produce large amounts of lactic acid as the end products of sugar fermentation. This creates an acidic environment which is not suitable for many bacterial strains.

F. ViroShield™: Prevention of pathogen binding to host cells will prevent infection Since viruses require binding to a receptor on the target cell surface for infection, strategies directed at inhibiting the interaction of a virus with its host receptor should be effective at preventing infection. The use of a bacterial shield against viral pathogens on mucosal surfaces is termed a ViroShield™.

The concept of the ViroShield™ type bacteria can be illustrated by the viral agents causing the common cold. The viral agents for the common cold are mainly consisting of the rhinovirus major group which bind to the ICAM-1 receptor in humans. Soluble ICAM-1 molecules expressed through recombinant DNA technology have been found to be effective in inhibiting HRV binding to susceptible cells and preventing infection (Martin, S., et al., *Antimicrob Agents Chemother*, 37(6):1278–84, 1993, hereinafter Martin, et al., 1993).

Approximately 60 ICAM-1 molecules can bind to a single HRV virion (Hoover-Litty, H. and Greve, J. M., *J Virol*, 67(1):390–7, 1993). This correlates with the fact that the HRV capsid is an icosahedral complex composed of 60 copies of each of the viral coat proteins (Smith, T. J., et al., *J Virol*, 67(3):1148–58, 1993). The actual receptor binding site on the HRV capsid was found to be a surface depression or "canyon" by X-ray crystallography (Oliveira, M. A., et al., *Structure*, 1 (1):51–68, 1993). This canyon is sufficiently small in size such that antibody molecules cannot fit, and this is one reason why humans are susceptible to repeated infections by HRV since the virus is resistant to antibody binding at this key neutralization site.

After binding to ICAM-1, a conformational change is induced in the capsid which causes the release of the viral RNA into the host cell (Martin, et al., 1993). Soluble ICAM-1 molecules are relatively ineffective at inducing capsid conformational change and thus functional inactivation of virions (Martin, et al., 1993, and Crump, C. E., et al., *Antimicrob Agents Chemother*, 38(6):1425–7, 1994 hereinafter Crump, et al., 1994); however, chimeric molecules combining the HRV-binding domains (1 and 2) of ICAM-1 and constant regions of immunoglobulin (Ig) molecules (IgA, IgG, or IgM) showed some effect. This effect is thought to be due to the ability of chimeric molecules to dimerize (IgA and IgG) or multimerize (IgM) via the association of the Ig domains. Multimeric receptors more closely resemble the natural state on cell surfaces, where several immobilized receptors binding to a virion may induce conformational distortion to the capsid to cause vital RNA release.

Expression of ICAM-1 on the external surface of mucosal bacteria is an extension of the multimeric-molecule strategy, with key additional benefits. Since bacteria are considerably larger than viral particles, bound HRV should be readily immobilized onto the bacterial surface. A key advantage of this invention is that only a few ICAM-1 receptors must be bound in order to effectively immobilize and neutralize a virion, whereas strategies involving soluble ICAM-1 molecules potentially must cover all 60 binding sites in order to ensure complete neutralization of a single virion. Furthermore, ICAM-1 molecules on bacterial surface are efficient in inducing capsid conformational change because simultaneous binding of several ICAM-1 molecules immobilized on a bacterial surface to several faces of a vital capsid will distort the geometry of the viral capsid and lead to conformational change and premature viral RNA release.

Viral RNA released into the bacteria are readily degraded by the abundant nucleases within bacterial cytoplasm. This leads to irreversible inactivation of viral particles, which is a key advantage of this invention because binding itself is a reversible process, and binding of soluble ICAM-1 molecules, chimeric molecules, or other drugs to HRV without functional inactivation would still leave a significant fraction of viral particles free to bind host cells at any given time. With ViroShield™ type mucosal bacteria, each bacteria is capable of irreversibly inactivating a large number of viral particles, ensuring that the majority of any vital inoculum would be eliminated before they can infect underlying host cells.

Accordingly, soluble CD4 molecules have also been shown to be effective in binding and preventing infection of HIV to target cells in vitro (Orloff, S. L., et al., *J Virol*, 67(3):1461–71, 1993). However, results of clinical trials with intravenously administered soluble CD4 molecules have been disappointing (Moore, J. P., et al., *Aids Res Hum Retroviruses*, 9(6):529–39, 1993). The reason is not due to lower binding affinity of primary vs. laboratory isolates of HIV to soluble CD4, but rather that primary isolates are less prone to inactivation after binding to soluble CD4 (Ashkenzai, A., et al., *Proc Natl Acad Sci*, 88:7056–7060, 1991 and Turner, S., et al., *Proc Natl Acad Sci USA*, 89(4):1335–9, 1992).

The expression of CD4 on bacterial surfaces should facilitate irreversible inactivation of all strains of HIV. In particular, CD4 expression on the surface of Lactobacilli on the vaginal mucosa would be effective at preventing HIV infection through vaginal intercourse. *E. coli* similarly transformed would be effective against HIV transmission via rectal intercourse.

An important point to keep in mind is the distinction between infection and clinical disease. For any pathogen, there is a minimum inoculating dose necessary to cause clinical symptoms from an infection. Exposure to an inoculum below this dose normally does not lead to clinical disease. Therefore, to successfully prevent disease, a strategy does not necessarily need to inactivate every particle of an inoculating dose of a virus, but rather to reduce the number of viable viral particles below the minimum infectious dose.

Since the ViroShield™ approach aims to prevent entry of a viral pathogen into a host, it not only prevents clinical disease, but should prevent infection altogether. Standard vaccines do not prevent entry of viral pathogens into a host. This may be important as certain viruses are known to trigger autoimmune processes in some hosts, regardless of whether they cause clinical infection.

Potential applications:

| Virus | Receptor | Portal of Entry | Suitable Bacterial Host |
|---|---|---|---|
| HRV | ICAM-1 | URT | URT flora- Strept gordonii or |
| Influenza | sialic acid | URT/LRT | Staph xylosus |
| Adenovirus | Vitronectin | URT | Strept or Staph |
| HIV | CD4 | vaginal mucosa | Lactobacillus |
| HSV 2 | heparin sulfate | vaginal | Lactobacillus |

G. Neutralization of pathogens upstream of their infection site

The only mucosal surfaces in the body relatively free of bacterial colonization are that of the stomach, upper small intestines, and lower respiratory tract. A few important viruses infect at the upper small intestines, the most significant of which are rotavirus and poliovirus (Murray, et al., 1994). Since bacterial counts in this area are low, even if all of these bacteria express receptors for the virus, it may not be possible to completely inactivate an inoculating dose of that virus. However, to reach the small intestines, viral particles must first enter the oral cavity and travel through the esophagus both are heavily colonized by bacteria. Therefore, it may be possible that bacteria on oropharyngeal/ esophageal mucosal surfaces expressing viral receptors can absorb/inactivate enough viral particles to significantly decrease the infectious inoculum delivered to the small intestines.

Viruses that infect the lower respiratory tract include influenza, parainfluenza, and RSV (Murray, et al., 1994). Vital particles inhaled into respiratory tract via droplets will settle out along various portions of the respiratory mucosa depending on the physical properties of the virion, droplet, and flow. Engineered bacteria along these viruses' path through the URT may absorb/inactivate sufficient numbers of vital particles to reduce the inoculating dose reaching the lower respiratory tract below the minimum required for clinical disease.

H. Prevention of exit of pathogens to infect other uninfected hosts.

This invention also provides for a method of preventing the exit of the virus from an infected host. Preventing a pathogen from exiting an infected host would mean preventing spread of the pathogen to a number of uninfected individuals, which would be extremely important from a public health viewpoint. Rapid spread of a pathogen may wipe out entire villages in third world countries. ViroShield# should be useful even in already infected hosts by absorbing/ inactivating viral particles as they exit the host. Even if ViroShield™ is unable to prevent infection of rotavirus or poliovirus for reasons discussed above (section G), engineered bacteria in the colon may still absorb/inactivate viral particles before they exit the host.

I. Use of engineered bacteria in potentially-contaminated water to inactivated virions In third-world countries, viruses may be transmitted rapidly through inadequately treated water supplies. Fecalorally transmitted viruses, such as rotavirus, may exist in low titers in the drinking water of a village after contamination by a single infected individual, and go on to infect a number of uninfected individuals. Non-pathogenic bacteria expressing rotavirus receptors may be added to suspect water supplies to absorb/inactivate viral particles in these settings, as long as the ingestion of the engineered bacteria is not harmful to a host. This approach should be an effective and economical means of quickly controlling orally-transmitted viruses in third-world countries.

J. Sources of genes which confer virus-binding capacity

The capacity to bind a virus may be conferred onto a bacteria in at least three ways. The first is by making the bacteria express on its surface the normal host receptor for the virus, such as ICAM-1 for HRV (major group) and CD4 for HIV. These are normal human proteins and the complete sequences of many of these genes have been determined and are stored in the database GeneBank. An advantage to this approach is that it is not readily avoided by viral mutation. If the virus mutates such that it no longer binds to the receptor expressed on bacteria, it would also lose its ability to bind to its target cell and thus no longer be infectious.

The second method is by expressing an antibody fragment (or any peptide with the capacity to bind a specific target on the surface of the virus) on the bacterial surface against a conserved determinant on the viral surface, such as VP4 on poliovirus, or gp120 on HIV. Antibody fragments (and peptides) against essentially any antigen can now be selected from a phage-display library (Marks, J. D., et al., *J Biol Chem*, 267(23):16007–10, (1992)).

Once appropriate clones are found, the gene coding for the antibody fragments can then be isolated and used. In addition, it was recently found that enveloped viruses, in the process of budding out of a host cell, carry along on their envelope certain host surface proteins, such as HLA DR on HIV (Arthur, et al, *Science*, 258(5090):1935–1938, (1992)). Thus, the human HLA DR molecule is a normal constituent of the HIV envelope. Antibody fragments directed against a conserved epitope of the HLA DR molecule may be capable of binding all isolates of HIV, and would be particularly effective in preventing male-to-female HIV spread when expressed on the surface of bacteria on the vaginal mucosa, or HIV transmission via anal intercourse when the engineered bacteria is applied to the rectum.

The third means of binding a virus by a bacteria is through the expression of certain carbohydrate moieties on the bacterial surface. A number of viruses use carbohydrate moieties as the receptor for entry into a host cell. One prominent example is the influenza virus which binds to sialic acid. Bacteria may be made to produce the enzyme sialic acid transferase in its cytoplasm which would lead to addition of sialic acid residues on normal surface proteins, thus causing influenza viruses to bind to said bacteria. The complete gene sequences of many bacterial carbohydrate transferases are known and appear in the literature.

K. Expression Systems for surface expression in bacteria

The expression of heterologous proteins on the surface of bacteria generally takes advantage of the normal surface proteins of the bacteria. It is becoming known that certain sequences within proteins direct them for export out of the bacterial cytoplasm, while others help to anchor a protein to the cell membrane. Hybrid proteins are created in which a heterologous protein sequence replaces the exposed portion of a normal surface protein, leaving the localization signal sequences intact. Several outer membrane proteins have been exploited as targeting vehicles for the localization of heterologous proteins, including the *E. coli* outer membrane protein maltoporin (LamB), *E. coli* pilin proteins K88ac and K88ad, *E. coli* outer membrane porins PhoE, OmpA, and OmpC, and the *S. typhimurium* Flagellin and TraT lipoprotein (U.S. Pat. No. 5,348,867).

A more detailed discussion of surface expression of proteins on the surface of gram-negative bacteria may be found in U.S. Pat. No. 5,348,867, and for gram-positive bacteria in PCT WO 93/18163.

1. Construction of Vectors

Plasmids are circularized DNA molecules commonly found in bacteria. They replicate independently from the bacterial host genome via an origin of replication (ori) site. Genes inserted into a plasmid are readily transcribed if placed downstream of appropriate promoter sequences. Certain promoter sequences exist which are regulated by external factors such as the molecule IPTG. A number of plasmids have been optimized for individual bacterial host strains, most notably *E. coli*. Plasmids have been constructed for surface expression of heterologous proteins in *E. coli* (e.g. pTX101 as described in U.S. Pat. No. 5,348,867), Streptococcus gordonii (e.g. pVMB20-GP232 transformation system, as described in PCT/US93/02355), and others. Both systems contain a signal sequence which directs a polypeptide to the cell surface, with an insert site for the desired heterologous gene, and an antibiotic resistance gene to help in selection of transformed bacteria. Other suitable streptococci include the lactic streptococci which have been widely transformed (De Vos, *FEMS Microbiology Reviews*, 46:281–295 (1987)).

Starting from the appropriate vector plasmid for each selected bacterial host, the plasmid will be digested with appropriate restriction enzymes to expose the cloning site. Then the desired heterologous gene will be ligated into the plasmid.

2. Transformation of bacterial cells

Appropriate bacterial host strains are selected for individual pathogens, heterologous protein or molecule, mucosal surface, and expression plasmid combination. The bacterial host will be rendered competent for transformation using standard techniques, such as the rubidium chloride method. Once transformed with the recombinant plasmid containing the desired heterologous gene, the bacteria will be grown in the appropriate media (e.g. LB media with 0.2% glucose). Transformed bacteria will be selected by adding the antibiotic to which the plasmid contains a resistance gene such that only transformed bacteria would survive.

3. Demonstration of expression of desired heterologous molecule on bacterial surface Expression of the heterologous gene can be constitutive or induced by stimulating the promoter to which it is attached, such as with IPTG. Surface expression of the heterologous molecule will be demonstrated by staining the bacteria with fluorescent-labeled antibodies against the desired molecule, looking for a surface fluorescence pattern. Furthermore, binding of the target pathogen by the transformed bacteria can be demonstrated by fixing the transformed bacteria onto a slide, incubating with the target pathogen, then staining with fluorescent antibodies against the target pathogen in one color (e.g. red), and against the transformed bacteria in another color (e.g. green), showing that the target pathogens (red) are closely associated with the transformed bacteria (green).

L. Irreversible inactivation of bound viruses

To ensure inactivation of the virus after binding to the transformed bacteria, the process of binding must trigger concomitant release of viral genetic material. In this way, bacterial nucleases can degrade the viral genetic material, thus irreversibly inactivating the virus. Many viruses, such as HRV, release their genetic material after binding to immobilized receptors on the target cell surface through a conformational shift of the viral capsid (Martin, et al., 1993). This situation should be successfully mimicked by expression of the receptor on the surface of bacteria. Some viruses, such as HIV and influenza, contain fusogenic domains in their coat proteins which facilitate release of genetic material after binding (Murray, et al., 1994). Different mechanisms are engineered into bacteria to ensure release of genetic material and thus irreversible inactivation of specific viruses.

M. Successful Colonization of Engineered Bacteria

Colonization of mucosal membranes with non-recombinant bacteria is well-known. It was optimally achieved by co-administering antibiotics along with bacteria resistant to that antibiotic (Freter, R., et al., *Infection and Immunity*, 39(2):686–703, 1983). Under normal conditions colonization disappears within 1–2 weeks after antibiotics are discontinued, as the resident microflora recovers and reestablishes itself (Bennet, et al., 1992). To enhance colonization the following three methods are suggested.

The first method is to repetitively select for rapid colonizing bacteria on animal or human mucosal layers. For example, one would apply a wildtype bacterial strain to a mucosal surface and repetitively isolate and in vitro culture bacteria, returning at each step to the mucosal surface. Ultimately, an enhanced colonizing bacterium is obtained.

The second method is to have the recombinant bacteria express fusion proteins on their surface, which consist of a virus-binding domain and a host-binding domain. The host-binding domain will allow the bacteria to bind to certain determinants (protein or carbohydrate) on a selected host mucosal surface with high affinity, thus conferring the bacteria a slight survival advantage over the resident microflora. This has the added advantage of ensuring continued co-expression of the virus-binding domain, which would otherwise serve the bacteria no intrinsic survival benefit and therefore its expression may otherwise dwindle with time.

The third method is to induce the already resident microflora themselves to express the virus-binding protein by introducing the gene via bacteriophage. Bacteriophage has been used successfully to introduce genetic material into bacteria for some time. A number of bacteriophage vectors have been developed for different bacteria. Lactobacillus is likely the most suitable strain for vaginal mucosa and bacteriophage vectors optimized for lactobacillus are available for this invention. A bacteriophage vector has recently been developed for *Lactobacillus gasseri* based on the temperate bacteriophage ϕadh (Raya, R. R., et al., *J Bacteriology,* 174(17):5584–5592, 1992 and Fremaux, C., et al., Gene, 125:61–66, 1993). This vector undergoes site-specific integration into the host chromosome at defined phage (attP) and bacterial (attB) attachment sites. Optionally, the fusion gene may be placed under control of a strong promoter optimized for lactobacillus into the vector, along with a 'suicide' gene under control of an inducible promoter.

Certain agents may also be added to a unit dose of the bacteria to aid in colonization. Many bacteria on mucosal surfaces secrete capsular materials which coalesce to form a biofilm which covers the entire mucosal surface. It may be beneficial to add an enzyme which digests this biofilm material to promote penetration of the engineered bacteria into the biofilm for more successful colonization. The enzymes include DNAses, peptidases, collagenases, hyaluronidases, and other carbohydrate degrading enzymes. Antibiotics (to which the engineered bacteria itself is not susceptible) may also be added to decrease the number of resident bacteria on the mucosal surface in order to make room for the engineered bacteria.

N. Persistent Expression of Heterologous Protein

As mentioned above, theoretically, expression of a foreign gene which serves a bacteria no purpose would likely dwindle over time, and the foreign gene would eventually be lost (Cardenas, L. and Clements, J. D., *Vaccine,* 11(2):126–135, 1993). To enhance persistent expression of the heterologous protein construct, an incentive may be created for the bacteria to express the gene. One way is the approach outlined above: create a fusion protein with virus-binding and host-binding domains so that the host-binding capability would confer a selective advantage to the bacteria to ensure the fusion proteins persistent expression. Another approach may be to create an internal requirement for the heterologous protein such that transformed bacteria that stop expressing the protein would die.

0. Vehicles for delivery/dosing regimen

Delivery of engineered bacteria to a desired mucosal surface depends on the accessibility of the area and the local conditions. Engineered bacteria may be placed in a saline solution for delivery to the naso- and oropharynx, or in a foam for delivery onto the vaginal or rectal mucosa. Mucosal surfaces less readily exposed—e.g. esophagus and trachea—may require a more viscous vehicle such as glycerin or sugar which facilitates the coating of the lining as it travels down the tract. Access to the small intestines and colon will require survival through the acid conditions of the stomach, hydrolytic enzymes secreted by the pancreas, and the antimicrobial effects of bile. Protective capsules have been suggested for protecting bacteria through the upper GI transit (Henriksson, A., et al., *Appl Environ Microbiol,* 57(2):499–502, 1991, hereinafter Henriksson, et al., 1991). It has been found that some strains in the colonic flora are inherently capable of surviving these conditions and therefore would be suitable for use in the GI tract.

Bacteria are self-replicating, so theoretically if an engineered bacteria successfully colonizes a mucosal surface, it should persist indefinitely. However, numerous factors may limit the indefinite survival of an engineered bacterial population on a given mucosal surface, the most significant factor being the fierce competition for space by a number of different bacteria on any mucosal surface. Therefore, it is envisioned that applications of engineered bacteria to a mucosal surface will need to be repeated on a regular basis; optimal dosing intervals are routine to determine, but will vary with different mucosal environments and bacterial strain. The dosing intervals can vary from once daily to once every 2–4 weeks. Oral administration of $10^8$–$10^{11}$ viable bacteria has produced transient colonization of colonic mucosa (Henriksson, et al., 1991 ). It is expected that colonization of the URT and vaginal mucosa will require less, as low as $10^6$ viable bacteria, since these surfaces are more directly accessible and do not pose the acid and other harsh conditions of the upper GI tract.

To deliver genes directly into bacteria already resident on a mucosal surface, bacteriophage which specifically infect a selected bacteria will be used as the vector. Bacteriophage are viruses which infect bacteria. Examples include bacteriophage lambda, M13, and T7 which all infect *Escherichia coli,* and ϕadh which infects *Lactobacillus gasseri.* The nucleic acid of the selected bacteriophage may be manipulated such that the heterologous gene(s) replaces the genes coding for bacteriophage coat proteins, rendering the bacteriophage replication-defective. Adding these recombinant DNA molecules into cell lysates containing functional bacteriophage proteins will lead to assembly of functional bacteriophage particles carrying the heterologous gene(s). These replication-defective bacteriophage particles can then be introduced onto a desired mucosal surface to infect selected floral bacteria. The typical dosage would be $10^8$ to $10^{12}$ PFU/ml applied to the mucosal surface. The proportion of solution to the treated surface should approximate 0.1 to 1.0 ml per square centimeter of mucosal surface. The vehicle would be similar to the vehicle described above for the bacteria.

P. Situations particularly suited for this invention

1. To prevent infection from viruses for which no effective vaccine is presently available: HIV, HPV, HSV, Hepatitis A Virus, Varicella Zoster Virus (chickenpox), Rotavirus, etc.

2. Any individual who wants to minimize his/her risk of contracting viral URIs/influenza, especially those who travel frequently, work at public places (healthcare providers, school teachers, etc.), have young children, and those with important upcoming events who cannot risk being ill.

3. Immunosuppressed individuals-since ViroShield™ represents a completely additional layer of protection on the mucosal surfaces, it does not rely on normal function of the immune system, and in fact should work in conjunction with the immune system.

4. Third world countries where administration of vaccines may be difficult and unreliable; ViroShield™ against rotavirus would be particularly useful in these situations.

5. Individuals with allergic reactions to certain components in a vaccine preparation, such as eggwhite proteins in the preparation of the flu vaccine.

6. Individuals traveling to third-world countries where certain viruses are endemic, such as Hepatitis A and Poliovirus.

7. Individuals with significant risk factors for sexually-transmitted diseases.

8. Protection of livestock animals from pathogenic viral infection.

Q. Definitions

Bacteria: Minute, unicellular prokaryotic organisms that are classified as lower protists. They may occur as symbionts, parasites, or pathogens of humans and other animals, plants, and other organisms. Most of the mucosal surfaces of humans and animals are heavily colonized by a wide variety of bacteria, which serve a number of useful functions to the host.

Biofilm: A complex network of different bacteria and extracellular matrix materials secreted by the bacteria which become confluent as a film on many mucosal surfaces.

Colonize: As applied to the bacterial flora, a state in which a bacteria resides harmlessly on a host mucosal surface. The residency time may be from 2 days to permanent, but more typically 1 week to 1 month.

Conserved determinant: The portion of a protein which is common amongst many variants of the protein. This is important in viruses because there are often numerous strains of a single virus, each with slightly different variations in the viral proteins. A conserved determinant on a viral protein refers to an epitope which is common in all strains of the virus.

Disease: As applied to a viral infection, this is a state in which a host suffers harmful effects from a viral infection, either immediate (e.g. fever, chills, bodyaches, etc.) or long-term (e.g., chronic hepatitis and hepatocellular carcinoma from chronic hepatitis virus types B and C infections, and cervical cancer from chronic HPV infection).

Fusion: As used in this document, refers to the act of merging of two membranes such that the contents of the two entities combine into a single unit.

Genetic material: Generally DNA which contains at least one gene and the regulatory elements which affect the expression of that gene.

Host receptor: A molecule on the surface of the host (target) cell to which a virus attaches in order to gain entry into the host cell.

Hosts: The hosts include both animals and humans. The invention is useful for protecting livestock animals including mammals and birds.

Inactivation: The process of rendering an infectious agent no longer capable of infecting a host.

Mucosal surface: The epithelial membranes which line the inner interface of the body with the environment, including the respiratory tract, gastrointestinal tract, and genitourinary tract.

Receptors: As applied to viral receptors include the native protein and the functional domains that provide the specific binding characteristics that define these proteins as receptors of virus binding.

Selected for its ability to colonize the mucosal layer: As applied to bacteria refers to bacteria which have been chosen by either selective pressure or by deliberate genetic transformation to enhance ability to colonize mucosal surfaces. The ability whether in terms of absolute numbers or in residency time is defined as at least double the wildtype's ability to colonize.

Selective advantage: Certain features which when conferred upon a bacteria cause the bacteria to be better adapted to survive in a specific environment such that it will have a greater chance than other bacteria in the same environment to survive and flourish in that environment.

Transform: As applied to bacteria, the introduction of foreign genetic material into a bacteria for the purpose of causing said bacteria to express the foreign gene(s).

Viral infection: The introduction of a virus into a host or a host cell. This does not necessarily suggest harmful effects suffered by the host and needs to be distinguished from clinical disease. This is an important concept since ViroShield™ represents a way to prevent infection altogether, while standard vaccines do not actually prevent infection but may prevent disease.

Virus: An infectious agent that consists of proteins and genetic material, either DNA or RNA, both of which are arranged in an ordered array and are sometimes surrounded by an envelope. A virus is generally smaller than a bacterium and is an obligate intracellular parasite at the genetic level; it uses the cell machinery to produce viral products specified by the viral nucleic acid. They are classified into 5 classes based on the type of nucleic acid (ssDNA, dsDNA, dsRNA, +strand RNA, −strand RNA), and a sixth class which is capable of reverse-transcribing +RNA into DNA (retroviruses, e.g. HIV).

All publications and patent applications cited in this specification are herein incorporated by reference as if each individual publication or patent application were specifically and individually indicated to be incorporated by reference.

EXAMPLES

The following examples are provided by way of illustration only and not by way of limitation. Those of skill will readily recognize a variety of noncritical parameters which could be changed or modified to yield essentially similar results.

A. The following examples teach the expression of the receptor for HRV, major group, ICAM-1, on the surface of *Esherichia coli*.

1. Expressing ICAM-1 domain on the surface of *E. coli* using

ICAM-1 domains 1 and 2 (the minimal receptor for HRV, major group) are expressed on the surface of *E. coli* through the creation of a fusion protein with aa 1–9 of normal surface protein Lpp and aa 46–159 of OmpA using a system described in U.S. Pat. No. 5,348,867. The DNA segment coding for domains 1 and 2 of ICAM-1 will be amplified using polymerase chain reaction (PCR) with primers designed to introduce in-frame EcoRI restriction sites flanking aa 1–168 of ICAM-1.

Plasmid TX101, as described in U.S. Pat. No. 5,348,867, contains the β-lactamase gene spliced into an EcoRI site, which is removed by EcoRI digestion followed by separation of the linearized plasmid and the β-lactamase gene with agarose electrophoresis. The PCR amplified ICAM-1 gene segment is ligated to the purified plasmid. *E. coli* strain JM109 is rendered competent by the rubidium chloride method and transformed with the pTX101-ICAM construct using electroporation.

The Lpp-OmpA-ICAM construct is under the control of the strong lpp promoter, which is inducible by IPTG (isopropyl thiogalactoside). Thus, IPTG stimulation will lead to high-level expression of the fusion protein. Transformed bacteria will be grown at 24° C. as this expression system works best (highest surface expression) at that temperature.

2. Ascertaining surface expression of ICAM-1 and demonstrating HRV binding.

Immunofluorescence is used to confirm proper ICAM-1 expression on the bacterial surface. Transformed bacteria are applied to a glass slide and fixed with methanol. Slides will be treated with murine mAbs against ICAM-1, washed extensively, then reacted with goat-anti-mouse IgG conjugated with rhodamine.

Fluorescence is observed under a Confocal Fluorescence Imaging System MRC-500 Bio-Rad microscope. To demonstrate HRV binding to the transformed bacteria, slides with fixed bacteria are incubated with HRV, washed extensively, then reacted with murine mAbs against HRV coat protein. After washing, the slides will be treated with goat-anti-mouse IgG conjugated with rhodamine and visualized as described above.

3. Neutralization of HRV infection of HeLa cells by transformed bacteria in in vitro assay.

Early infection of HeLa cells in vitro by HRV will be monitored by detecting HRV mRNA inside infected HeLa cells by Northern blot analysis. A semipermeable membrane with pores of sufficient size to allow passage of HRV but not bacteria or HeLa cells is placed on top of a monolayer of HeLa cells in a tissue culture flask. Transformed or unmodified bacteria are layered onto the semipermeable membrane, then HRV is added on top of the bacteria and allowed to infect the underlying HeLa cells.

After an appropriate amount of time for infection, (2–6 hrs), the bacteria and semipermeable membrane are removed, and the HeLa cells washed extensively. The cells are then lysed, and their total RNA isolated for Northern analysis which is a standard method useful for detecting HRV mRNA which is an indication of infection.

4. Methods of formulating transformed bacteria in an appropriate vehicle (foam, DNAse, etc.) for use in animal and human hosts:

Transformed bacteria are formulated in a number of vehicles for animal application, For use in the nasopharynx, transformed bacteria may be mixed in saline and applied as a nasal spray. The bacteria are added to the saline at concentration of $10^6$ to $10^8$ cells/ml and applied twice daily in a directed spray of 0.1 ml solution/$cm^2$ area of nasal mucosa.

B. The expression of a viral receptor on the surface of *Streptococcus gordonii.*

The following examples teach the expression of ICAM-1 on the surface of a gram-positive bacteria, since gram-positive bacteria are prominent members of the nasopharyngeal flora. The expression system is based on the one described in patent PCT/US93/02355. The examples provided herein use *Streptococcus gordonii,* but are readily adaptable to other gram-positive bacteria due to a common motif, LPXTGX, which allows the anchoring of proteins on the surface of essentially all gram-positive bacteria.

1. Expression of ICAM-1 on the surface of *Streptococcus gordonii.*

*S. gordonii, strain GP*232 described by Fischetti et al. in WO 93/18163 is used. In this strain, the gene which encodes for the M6 surface protein of *S. pyogenes* (contains the LPXTGX motif), emm-6.1, and an ermC gene (erythromycin resistance) disrupted by a cat (chloramphenicol acetyltransferase) gene have been inserted into the chromosome of GP232 downstream of a strong chromosomal promoter. GP232 expresses M6 on its surface, and is susceptible to erythromycin. Integration vector pVMB20 constructed by Fischetti et al. allows for the insertion of heterologous DNA sequences into emm-6.1. pVMB20 contains a functional (undisrupted) ermC gene, and is a 6.3-kb *E. coli* plasmid which does not replicate in *S. gordonii.* pVMB20 is digested with KpnI and HindIII to release a 538-bp KpnI/HindIII segment within emm-6.1, but leaving the LPXTGX motif intact. The ICAM-1 gene is PCR amplified using amplification primers specially designed to obtain an in frame KpnI/HindIII insert containing domains 1 and 2 of ICAM-1. The insert is then ligated into the digested vector.

Nucleotide sequence analysis of the pVMB20:ICAM-1 construct confirms the proper (in frame) insertion. The plasmid will be linearized and used to transform GP232 by standard methods. Homologous recombination between the 5' end of the emm-6.1 gene and the 3' end of the ermC gene, present on both the GP232 chromosome and the plasmid, allows for the integration of the ICAM-1 gene and the functional ermC gene into the GP232 chromosome.

Transformants are selected by screening for erythromycin-resistance, in media containing 5 μg/ml erythromycin.

2. Ascertaining surface expression of ICAM-1 and demonstrating HRV binding.

As in example A2, surface expression of ICAM-1 is verified by immunofluorescence using antibodies specific for ICAM-1. HRV binding will also be demonstrated as in example A2.

3. Neutralization of HRV infection of HeLa cells by transformed bacteria in in vitro assay.

Neutralization of HRV infection of HeLa by transformed GP232 will be demonstrated as in example A3.

C. Antibody expression on a *E. coli.*

The following examples teach the expression of an antibody fragment against a conserved determinant on the HLA DR molecule on the surface of *E. coli.* Since the HIV envelope is found to contain approximately 375 copies of the HLA DR molecules from its host (Arthur, L. O., et al., *Science,* 258(5090):1935–8, 1992.) an antibody fragment against a conserved determinant on HLA DR will bind to all isolates of HIV.

A phage display system exists which allows for the rapid selection of antibody fragments against essentially any target (Marks, J. D., et al., *J Biol Chem*, 267(23):16007–10, 1992.) is utilized to select for an antibody fragment with high affinity against a conserved determinant on HLA DR.

1. Selection for an antibody fragment with high affinity against a conserved determinant on HLA DR.

A phage library consisting of approximately $10^{14}$ bacteriophage each displaying a unique antibody fragment (scFv) on its surface is used (E.g., G. Winters, MRC, Cambridge, UK). Phage binding to HLA DR is selected by taking advantage of the fact that activated T cells express HLA DR, while resting T cells do not. All phage that bind activated T cells will be selected, then of this population, phage that bind resting T cells are removed. This process effectively isolates the subpopulation of phage that bind to HLA DR, and a few T cell activation markers. B cells express HLA DR constitutively. Subjecting this subpopulation of phage to B cells allows for selection of anti-HLA DR phage only, because B cells do not express T cell activation markers.

Of the phage that bind HLA DR, the ones that bind to conserved determinants are selected by screening the subpopulation against B cells of a variety of HLA DR specificities, and selecting only the clones that bind to every B cell specificity. If more than one clone is identified, the one with the highest binding affinity is used. Binding affinities in excess of $10^{-8}$ to $10^{-12}$ are preferred.

2. Method of expressing an antibody fragment against a conserved determinant on HLA DR on surface of *E. coli* using plasmid pTX101.

The $V_H$ and $V_L$ domains of the selected scFv are cloned using suitable primers designed to introduce in-frame EcoRI restriction sites at the N-terminus of the $V_H$ and the C-terminus of the $V_L$. The PCR amplified gene segment is ligated into the EcoRI site of pTX101. JM109 bacteria are transformed with the plasmid, and surface expression of the fusion protein will be induced with IPTG at 20° C. as described in example 1.

3. Method of ascertaining surface expression of antibody fragment and demonstrating HIV binding.

Immunofluorescence is performed to confirm proper anti-DR scFv expression on the bacterial surface. Transformed bacteria are applied to a glass slide and fixed with methanol. Slides are treated with soluble human HLA DR molecules, washed, murine mAbs against HLA DR, washed, then reacted with goat-anti-mouse IgG conjugated with rhodamine. Fluorescence will be observed under a Confocal Fluorescence Imaging System MRC-500 Bio-Rad microscope. To demonstrate HIV binding to the transformed bacteria, slides with fixed bacteria are incubated with HIV, washed extensively, then reacted with murine mAbs against the HIV coat protein gp120. After washing, the slides are treated with goat-anti-mouse IgG conjugated with rhodamine and visualized as described above.

4. Neutralization of HIV infection of T cells by transformed bacteria in in vitro assay Early infection of CEM cells (a laboratory T cell line) in vitro by HIV is monitored by detecting reverse transcriptase activity within infected cells. A semipermeable membrane with pores of sufficient size to allow passage of HIV but not bacteria or CEM cells is placed on top of CEM cells in a tissue culture flask. Transformed or unmodified bacteria are layered onto the semipermeable membrane, then infective HIV is added on top of the bacteria and allowed to infect the underlying CEM cells. After an appropriate of time for infection, (i.e. 2–6 hrs), the bacteria and semipermeable membrane are be removed, and the CEM cells washed extensively. These cells are lysed, and their cytosolic contents assayed for reverse transcriptase activity as an indication of early HIV infection.

5. Methods of formulating transforming bacteria in appropriate vehicle (foam, DNAse, etc.) for use in animal or human hosts.

For the GI tract, transformed *E. coli* bacteria are cultured and added to a mixture of various fatty acids conventionally used for rectal administrations such as: hydrogenated cocoa nut oil, glycerin, hydrogenated palm kernel oil, or other suitable material for rectal administration. The bacteria is added to the excipients at a concentration of $10^6$ to $10^8$ cells per mg of excipient. Each suppository is between 3–8 grams.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of binding viral particles to non-host cells in a host to increase the minimum viral load necessary to infect the host said method comprising contacting a mucosal surface of the host with an amount of transformed bacteria sufficient to colonize the mucosal surface, said bacteria having been transformed with genetic material so as to confer upon the bacteria the capacity to bind the viral particles.

2. A method of claim 1 where the transformed bacteria expresses a polypeptide on its surface which serves as the host receptor for the virus.

3. A method of claim 2 where the bacteria are transformed with genetic material which directs surface expression of a protein with comprising an ICAM-1 domain, where the virus is a human rhinovirus, and the host is human.

4. A method of claim 2 where the bacteria are transformed with genetic material which directs surface expression of a protein with a CD4 receptor, the virus is a human immunodeficiency virus, and the host is human.

5. A method of claim 2 where the bacteria are transformed with genetic material which directs surface expression of a protein with a poliovirus receptor, the virus is a poliovirus, and the host is human.

6. A method of claim 2 where the bacteria are transformed with genetic material which directs surface expression of a protein with a human complement receptor 2, the virus is an "epstein-barr" virus, and the host is human.

7. A method of claim 1 where the transformed bacteria expresses on its surface an antibody fragment against a conserved determinant on the virus.

8. A method of claim 7 where the bacteria are transformed with genetic material which directs surface expression of an antibody fragment against a monomorphic determinant of the human HLA DR molecule, the virus is a human immunodeficiency virus, and the host is human.

9. A method of claim 7 where the bacteria are transformed with genetic material which directs surface expression of an antibody fragment against a conserved determinant on the rotavirus coat protein, the virus is a rotavirus, and the host is human.

10. A method of claim 7 where the bacteria are transformed with genetic material which directs surface expression of an antibody fragment against a conserved determinant on the herpes simplex virus coat protein, the virus is a herpes simplex virus, and the host is human.

11. A method of claim 7 where the bacteria are transformed with genetic material which directs surface expression of an antibody fragment against a conserved determinant on the human papilloma virus coat protein, the virus is a human papilloma virus, and the host is human.

12. A method of claim 7 where the bacteria are transformed with genetic material which directs surface expression of an antibody fragment against a conserved determinant on the adenovirus coat protein, the virus is an adenovirus, and the host is human.

13. A method of claim 7 where the bacteria are transformed with genetic material which directs surface expression of an antibody fragment against a conserved determinant on the respiratory syncytia virus coat protein, the virus is a respiratory syncytia virus, and the host is human.

14. A method of claim 7 where the bacteria are transformed with genetic material which directs surface expression of an antibody fragment against a conserved determinant on the corona virus coat protein, the virus is a corona virus, and the host is human.

15. A method of claim 7 where the bacteria are transformed with genetic material which directs surface expression of an antibody fragment against a conserved determinant on the capsids of a virus selected from the group consisting of: cytomegalovirus, coxsackievirus, echovirus, hepatitis A virus and parainfluenza virus.

16. A method of claim 1 wherein the bacteria has a cell membrane and the virus has an envelope, wherein the transformed bacteria causes fusion between its cell membrane and the envelope of the virus.

17. A method of claim 16 wherein the transformed bacteria fuses with bound viral particles through a fusogenic domain engineered into the virus-binding polypeptide.

18. A method of claim 1 wherein the transformed bacteria is conferred sufficient selective advantage over other resident bacteria to allow said transformed bacteria to successfully colonize and survive indefinitely on a selected mucosal surface.

19. A method of claim 18 wherein the transformed bacteria is conferred enhanced ability to adhere to a host mucosal surface through a domain in the heterologous protein which binds to a determinant on a selected mucosal surface.

20. A method of claim 1 where the mucosal surface is the nasopharynx, oropharynx, esophagus, small intestines, large intestines, rectum, vagina, or penis.

21. A method of claim 1 where the transformed bacteria is resistant to an antibiotic and is co-administered with said antibiotic to enhance colonization of the transformed bacteria.

22. A method of claim 1 where the transformed bacteria is co-administered with an enzyme which degrades the mucosal surface to enhance colonization of the transformed bacteria.

23. A method of claim 22 wherein the enzyme is DNAse, peptidase, collagenase, hyaluronidase, or other carbohydrate degrading enzymes.

24. A method of claim 1 where transformed bacteria are applied to a mucosal surface through the use of a liquid solution, foam, suppository, sponge, or capsule.

25. A method of inhibiting an infection transmitted through vaginal intercourse by the application of transformed bacterial into the vaginal vault at the time of intercourse that binds and inactivates an infectious agent.

26. A method of claim 25 wherein the bacteria inactivate a pathogen selected from the group consisting of: HIV, HPV, HSV, gonorrhea, syphilis and chlamydia.

27. A method of claim 25 where the transformed bacteria are administered in the form of a vaginal foam or sponge, and may be administered in conjunction with other agents such as nonbacteriocidal spermicides.

28. A method of preventing the spread of a viral pathogen from an infected individual to others with transformed bacteria by administering an amount of bacteria sufficient to colonize the mucosal surfaces of the infected individual wherein said bacteria bind and inactivate infectious viral particles exiting the infected host.

* * * * *